United States Patent [19]
Sebillotte-Arnaud

[11] Patent Number: 5,814,322
[45] Date of Patent: Sep. 29, 1998

[54] GELLED COSMETIC AND/OR DERMATOLOGICAL COMPOSITION WHICH IS RICH IN SOLVENT AND WHICH CONTAINS HOLLOW PARTICLES, AND ITS APPLICATIONS

[75] Inventor: Laurence Sebillotte-Arnaud, Creteil, France

[73] Assignee: L'Oreal, Paris, France

[21] Appl. No.: 499,916

[22] Filed: Jul. 11, 1995

[30] Foreign Application Priority Data

Jul. 11, 1994 [FR] France ................... 94 08568

[51] Int. Cl.$^6$ ................ A61K 7/02; A61K 7/48
[52] U.S. Cl. ............ 424/401; 424/489; 424/497; 514/844; 514/846; 514/951
[58] Field of Search .............. 424/401, 78.03, 424/489, 497; 428/402; 514/944, 844, 846, 859, 860, 951

[56] References Cited

U.S. PATENT DOCUMENTS

| | | | |
|---|---|---|---|
| 4,944,937 | 7/1990 | McCall | 424/65 |
| 5,205,290 | 4/1993 | Unger | 128/653.4 |
| 5,223,559 | 6/1993 | Arraudeau et al. | 524/47 |
| 5,496,543 | 3/1996 | Lagrange et al. | 424/70.7 |
| 5,578,119 | 11/1996 | Short et al. | 106/287.35 |
| 5,593,680 | 1/1997 | Bara et al. | 424/401 |
| 5,637,291 | 6/1997 | Bara et al. | 424/59 |
| 5,728,389 | 3/1998 | Sebillotte-Arnaud | 424/400 |
| 5,738,841 | 4/1998 | Mellul et al. | 424/59 |

FOREIGN PATENT DOCUMENTS

A-0 614 656  9/1994  European Pat. Off. .

OTHER PUBLICATIONS

Kirk–Othmer, Encyclopedia of Chemical Technology, 3rd Edition. John Wiley & Sons. N.Y. vol. 21, pp. 106–131. (1983). Size Measurement of Particles.

Primary Examiner—Robert H. Harrison
Attorney, Agent, or Firm—Oblon, Spivak, McClelland, Maier & Neustadt, P.C.

[57] ABSTRACT

Gelled compositions containing a cosmetically and/or dermatologically acceptable hydrophilic medium, at least one gelling agent, and hollow particles, in which the medium contains at least 20% by weight of organic solvent, based on the total weight of the composition, and less than 50% by weight of water, based on the total weight of the composition, may contain an active agent which makes it possible in particular to prevent and/or control pigmentation of the skin or to control greasy skin and/or excessive weight.

22 Claims, No Drawings

GELLED COSMETIC AND/OR DERMATOLOGICAL COMPOSITION WHICH IS RICH IN SOLVENT AND WHICH CONTAINS HOLLOW PARTICLES, AND ITS APPLICATIONS

BACKGROUND OF THE INVENTION

1. Field of the Invention

The present invention relates to cosmetic and/or dermatological compositions which are rich in organic solvent and which contain hollow particles. Such compositions are provided in the form of white or colored gels intended for the specific care and/or treatment of the skin of the face or of the human body, including the scalp.

The present invention also relates to the use of this composition in the cosmetic treatment of the skin and in particular for preventing and/or controlling pigmentation of the skin or for controlling greasy skin and/or excessive weight.

The present invention also relates to the use of this composition for the preparation of a salve or ointment intended for the dermatological treatment of the skin and to a process for the cosmetic treatment of the skin.

2. Discussion of the Background

The compositions conventionally used in the cosmetic and/or dermatological fields are water-in-oil (W/O) emulsions, oil-in-water (O/W) emulsions or aqueous gels, in which it is often difficult, indeed even impossible, to incorporate certain active agents such as kojic acid, caffeic acid, salicylic acid and its derivatives, sunscreening agents, slimming agents, anti-free-radical agents, vitamins or insect repellents used in various types of treatment such as controlling ageing, acne, excessive weight or for promoting blood circulation and the like.

In general, these active agents have a tendency to recrystallize or to degrade. The result is a more or less significant loss in the efficacy of these compositions, according to the degree of recrystallization and/or degradation, which runs counter to the desired objective. In addition, this recrystallization or degradation can modify the overall stability of these compositions and their appearance, which can turn the user away from these specific treatment compositions. Moreover, to dissolve such active agents in some compositions often requires heating the latter, which is relatively troublesome for active agents which are sensitive to heat, such as vitamins, certain plant extracts or certain proteins.

For these W/O or O/W emulsions to be stable (non-separation of the aqueous and oily phases), it is necessary to use emulsifying agents (or surface-active agents). Unfortunately, such surface-active agents often irritate the skin. In addition, these emulsions often lack coolness on application, which can be harmful to their uses during hot times of the year and/or in hot countries. An aqueous gel is much more appreciated under these conditions of use, but the excessively large amount of water in aqueous gels does not make it possible to introduce the above-mentioned active agents therein.

There thus remains a need for a stable composition which has all the advantages of a gel, which can be used in the cosmetic and/or dermatological fields and which makes possible sufficient solubilization of the active agents generally used in these fields, for the purpose of maximum efficiency.

SUMMARY OF THE INVENTION

Accordingly, it is one object of the present invention to provide novel cosmetic and/or dermatological compositions.

It is another object of the present invention to provide cosmetic and/or dermatological compositions which exhibit the advantages of gels and which contain an active agent useful for preventing and/or controlling pigmentation of the skin or for controlling greasy skin and/or excessive weight.

It is another object of the present invention to provide a method for preventing and/or controlling pigmentation of the skin or for controlling greasy skin and/or excessive weight.

These and other objects, which will become apparent during the following detailed description, have been achieved by the inventor's discovery that a cosmetic and/or dermatological compositions containing a hydrophilic medium, at least one gelling agent, and hollow particles, in which the medium contains at least 20% by weight of organic solvent, based on the total weight of the composition, and less than 50% by weight of water, based on the total weight of the composition, solve the above-mentioned problems.

DETAILED DESCRIPTION OF THE PREFERRED EMBODIMENTS

The composition of the present invention has a certain consistency and/or behaviour; it is not free-running, that is to say that it does not form a string when taken with the finger. In addition, it is provided in the form of an oily and glossy, white or colored (in the presence of dyes) cream, which is an appearance much sought after by users.

The use of a gelled composition makes it possible to employ a large amount of solvent, which is difficult to achieve with a W/O or O/W emulsion: the introduction of solvent into an emulsion breaks up the latter.

The composition of the invention additionally has the advantage of contributing very great softness and great comfort on application. Thus, the presence of the particles makes it possible, inter alia, to introduce a large amount of fatty substances into the composition, without experiencing any greasy and/or sticky feeling.

The present composition, in contrast to the emulsions, contains nothing or very little in the way of surface-active agents. Moreover, in contrast to conventional processes for producing gelled or emulsified compositions, heating is not necessary to form the present composition. This therefore facilitates its manufacture and makes it possible to use active agents which are sensitive to heat, such as vitamins or plant extracts. The result is an improved efficiency with respect to the compositions obtained by heating.

The present composition is particularly well suited to dissolving active agents used in the cosmetic and dermatological fields. The composition of the present invention therefore additionally contains at least one active agent chosen in particular from depigmenting, keratolytic, slimming or anti-inflammatory active agents, active agents for treatment of acne or active agents intended for the treatment of greasy skin.

Mention may be made, as active agents which can be dissolved in the present composition, of depigmenting agents, such as caffeic acid or hydroquinone; agents active against greasy skin, such as retinoic acid and its derivatives, benzoyl peroxide, octopirox or keratolytic agents, such as salicylic acid and its derivatives, such as 5-(n-octanoyl) salicylic acid; anti-inflammatory agents, such as β-methasone 17-valerate, hydrocortisone or β-glycyrrhetinic acid; antibiotics, such as erythromycin and its derivatives or clindamycin and its derivatives; antifungal agents, such as miconazole or econazole; slimming agents, such as caffeine, centella asiatica or asiatic acid and its derivatives; active agents which stimulate hair regrowth, such as minoxidil; active agents which promote microcirculation, such as ruscus; or cooling active agents, such as menthol and camphor.

Although the amount of active agent in the present compositions is not particularly limited, good results may be achieved with compositions which contain from 0.01 to 25% by weight, preferably 0.1 to 10% by weight, of the active agent, based on the total weight of the composition.

The hydrophilic medium can preferably contain less than 30% of water, with respect to the total weight of the composition. Moreover, the pH of this hydrophilic medium can vary from 3 to 12 according to the gelling agent and/or active agents used.

It is possible to obtain a composition whose macroscopic appearance remains homogeneous and in which the active agent(s) do(es) not recrystallize and/or do(es) not degrade, in particular for at least 2 months at 45° C.

The gelling agent(s) is/are chosen from natural or synthetic polymers and polymer emulsions.

These are polymers or copolymers of unsaturated organic carboxylic acids or of unsaturated esters, polysaccharide derivatives, gums or polyvinyl-pyrrolidones and their derivatives.

The polymeric gelling agents are, for example: carboxyvinyl polymers or copolymers sold under the name Carbopol by the Company Goodrich, acrylic acid-stearyl methacrylate copolymers, poly(glyceryl methacrylate) sold under the name Lubrajel by the Company Guardian, or poly (glyceryl acrylate) sold under the name Hispagel by the Company Hispano Chimica.

The gelling agents which are provided in the form of W/O emulsions are, for example:

anionic copolymers whose general formula is described in Patent Application EP-A-0,503,853, cationic copolymers whose general formula is described in the document EP-0,395,282 of the Company Allied Colloids Limited. These polymers are, for example, sold under the name Salcare SC 90, Salcare SC 91, Salcare SC 92 or Salcare SC 95. It is also possible to use those sold under the name Bozepol C Nouveau, PAS 5194 or PAS 5193 by the Company Hoechst.

These gelling agents are used in the amounts commonly used to obtain a gel. For example, use is made, as active material, of 0.1% to 10% by weight of gelling agent, based on total weight of the composition, preferably of 1% to 8% by weight, more preferably 3% to 6% by weight.

The solvent(s) which can be used in the invention is/are hydrophilic solvents optionally in combination with lipophilic solvents or with both hydrophilic and lipophilic solvents. In particular, these solvents are cosmetically and/or dermatologically acceptable solvents (acceptable tolerance, toxicology and feel).

Hydrophilic solvents can represent from 5% to 90% of the total weight of the present composition, preferably from 20% to 70%, more preferably from 50% to 70%. These hydrophilic solvents are, for example, linear or branched lower monoalcohols having from 1 to 8 carbon atoms, such as ethanol, propanol, butanol, isopropanol or isobutanol; polyethylene glycols having from 6 ethylene oxide molecules to 80 ethylene oxide molecules; polyols, such as propylene glycol, isoprene glycol, butylene glycol, glycerol or sorbitol; mono- or dialkyl derivatives of isosorbide in which the alkyl groups have from 1 to 5 carbon atoms, such as dimethyl isosorbide; glycol ethers, such as diethylene glycol monomethyl or monoethyl ether, and propylene glycol ethers, such as dipropylene glycol methyl ether.

The composition of the present invention preferably contains at least 10% by weight of lower alcohols, based on the total weight of the composition.

Mention may be made, as solvents which are both lipophilic and hydrophilic, of polyols, such as isoprene glycol; polypropylene glycol (PPG) derivatives, such as esters of polypropylene glycol and a fatty acid or ethers of PPG and a fatty alcohol, such as PPG-23 oleyl ether and PPG-36 oleate. These solvents are used in combination with the hydrophilic solvents in an amount ranging from 0% to 50% by weight, based on the total weight of the composition, preferably from 0% to 30% by weight, more preferably from 0% to 10%.

It is optionally possible to use lipophilic solvents in combination with hydrophilic solvents and/or both hydrophilic and lipophilic solvents. These lipophilic solvents may be present in an amount of from 0% to 50% by weight, based on the total weight of the composition, preferably from 0% to 30% by weight, more preferably from 0% to 10%. These solvents are in particular fatty esters, such as diisopropyl adipate, dioctyl adipate, dioctyl malate, glyceryl isostearate, octyl acetostearate, cetyl octanoate or diisopropyl sebacate; or Guerbet alcohols (or 2-alkyl-1-alkanols) of general structure $R_1$—$CHR_2$—$CH_2OH$ with $R_1$ and $R_2$, which are identical or different, representing a hydrogen atom or an alkyl radical having from 1 to 10 carbon atoms, such as octyldodecanol, hexyldecanol or cyclododecanol.

The particles of the invention have, in particular, a density chosen within the range extending from 15 kg/m$^3$ to 200 kg/m$^3$, preferably not greater than 120 kg/m$^3$, for example from 40 kg/m$^3$ to 100 kg/m$^3$, and more preferably from 60 kg/m$^3$ to 80 kg/m$^3$. To obtain this low density, use is advantageously made of expanded polymer or copolymer particles, preferably based on acrylonitrile and on an acrylic or styrene monomer and/or on vinylidene chloride.

It is possible, for example, to use a copolymer containing: from 0% to 60% by weight of units derived from vinylidene chloride, from 20% to 90% by weight of units derived from acrylonitrile and from 0% to 50% by weight of units derived from an acrylic or styrene monomer, the sum of the percentages (by weight) being equal to 100. The acrylic monomer is, for example, a methyl or ethyl acrylate or methacrylate. The styrene monomer is, for example, α-methylstyrene or styrene.

The particles used in the present invention are preferably hollow particles of an expanded copolymer of vinylidene chloride and of acrylonitrile or of vinylidene chloride, of acrylonitrile and of methacrylate. These particles can be dry or hydrated.

The particles used in the present invention can be obtained, for example, according to the processes of Patents and Patent Applications EP-56,219, EP-348,372, EP-486, 080, EP-320,473, EP-112,807, and U.S. Pat. No. 3,615,972.

The internal cavity of the particles contains, in principle, a gas which can be air, nitrogen or a hydrocarbon, such as isobutane or isopentane.

The particles of the invention advantageously have a particle size ranging from 5 μm to 200 μm, preferably from 10 μm to 100 μm, more preferably ranging from 10 μm to 50 μm, even more preferably from 10 μm to 30 μm. As is understood in the art, particle size dimensions are average dimensions.

The particles which can be used in the invention are, for example, microspheres of the expanded terpolymer of vinylidene chloride, of acrylonitrile and of methacrylate sold under the trade name Expancel by the company Nobel Casco under references 551 DE 50 (particle size of approximately 40 μm), 551 DE 20 (particle size of approximately 30 μm and density of approximately 65 kg/m$^3$), 551 DE 12 (particle size of approximately 12 μm), 551 DE 80 (particle size of approximately 80 μm) or 461 DE 50 (particle size of approximately 50 μm). It is also possible to use microspheres formed from the same expanded terpolymer having a particle size of approximately 18 μm and a density of approximately 70 kg/m$^3$, known hereinafter as EL 23, or having a particle size of approximately 34 μm and a density of approximately 20 kg/m$^3$, known hereinafter as EL 43.

These particles additionally confer lightness and mattness on application on the emulsions containing them.

The compositions of the present invention may contain 0.1% to 10% by weight of such particles based on the total weight of the composition, preferably 0.5% to 5% by weight.

In order for the composition of the present invention to be more pleasant to use (softer on application, more nutritious or smoother), it is possible to add one or a number of oils which are soluble or insoluble in the hydrophilic medium, that is to say in water or the solvent.

Oils which are soluble in water or in aqueous/alcoholic medium may be present in an amount of from 0% to 50% by weight, based the total weight of the composition, preferably from 0% to 30% by weight, more preferably from 1% to 15% by weight.

Oils which are partially soluble in the solvent which can be used in the present invention are, for example, cyclomethicones (cyclohexa-, cyclopenta- or cyclotetradimethylsiloxane), linear volatile polydimethylsiloxanes (containing 2, 3, or 4 siloxane functional groups) or alternatively phenyldimethylsiloxanes.

Oils which are soluble in water which can be used in the invention are, for example, water-soluble silicones such as:

oxyethylenated polydimethylsiloxanes containing amide units, such as, for example, those sold under the name Silwax AX or Silwax DCA-100 by the company Siltech;

oxyethylenated polydimethylsiloxanes containing stearate groups, such as, for example, those sold under the name Silwax WD-IS by the company Siltech;

oxyethylenated polydimethylsiloxanes, such as, for example, those sold under the name Belsil DMC 6038 by the company Wacker;

stearoxypolydimethylsiloxanes, such as, for example, those sold under the name Belsil SDM 6022 by the company Wacker.

It is also possible to use oils which are insoluble in aqueous/alcoholic medium. These oils may be present in an amount of from 0% to 20% by weight, preferably from 1% to 15% by weight, based on the total weight of the composition. These insoluble oils are, for example:

mineral oils, such as liquid paraffin;

oils of animal origin, such as perhydrosqualene;

oils of plant origin, such as sweet almond oil, avocado oil, castor oil, olive oil, jojoba oil, sesame oil, groundnut oil, macadamia oil, grape seed oil, rapeseed oil, coconut oil, hazelnut oil, karite butter and its liquid fraction, palm oil, apricot kernel oil, calophyllum oil, rice bran oil, maize oil, wheatgerm oil, soybean oil, sunflower oil, evening primrose oil, safflower oil, passionflower oil, and rye oil;

synthetic oils, such as purcellin oil, fatty esters, including butyl myristate, isopropyl myristate, hexadecyl stearate, isopropyl stearate, octyl stearate, isocetyl stearate, decyl oleate, hexyl laurate, propylene glycol dicaprylate or glycol or glycerol octanoate, ricinoleates of mono- or polyfunctional alcohols (in particular cetyl alcohol), triglycerides of fatty acids, in particular of caprylic/capric acids or of saturated $C_{10}$ to $C_{18}$ fatty acids, esters derived from lanolic acid, such as isopropyl lanolate or isocetyl lanolate, isoparaffins, and fluorinated and perfluorinated oils.

The oils used can also contain one or a number of cosmetic and/or therapeutic lipophilic active agents, in particular those commonly used in the manufacture and production of cosmetic and/or pharmaceutical compositions. These active agents can be, for example, anti-free-radical agents; ceramides; sunscreening agents (in particular ultraviolet screening agents), such as 2-ethylhexyl para-methoxycinnamate, and in particular that marketed under the name "Parsol MCX" by the Company Givaudan, or 2-hydroxy-4-methoxybenzophenone, and in particular that sold under the tradename "Uvinul M40" by the Company BASF; insect repellents, such as n-butyl 3-cetylethyl-aminopropionate or N,N-diethylcaprylamide; slimming agents, such as D,L-α-tocopherol nicotinate, the oily extract of ginseng (Panax ginseng), the oily extract of English ivy (Hedera helix), the oily extract of dry flowers of arnica (Arnica montana L) and the oily extract of algae (Fucus vesiculosus). It is obvious that the above list of lipophilic active agents capable of being introduced into the composition of the present invention is in no way exhaustive.

The oils can also contain, depending on the envisaged application, one or a number of lipophilic formulation additives, such as preserving agents, antioxidants or emollients, scented oils or indeed even fragrances.

Other types of additives may also be present in the present composition, such as cellulose derivatives, such as carboxymethyl cellulose, hydroxymethyl cellulose or hydroxyethyl celluloses, sold under the name Idroramnosan, Liporamnosan or Alcoramnosan by the Company Vevy Europe, hydroxypropyl cellulose, sold under the name Veegum, and the like, as well as hydrophilic additives, such as moisturizers of the polyol type (glycerol or sorbitol). These derivatives may be present in an amount of from 0% to 5% by weight, based on total weight of the composition, preferably from 0.1% to 3% by weight, more preferably from 0.5% to 2%, and the polyols may be present in an amount of up to 10% by weight, preferably from 2% to 6%, based on the total weight of the composition.

The present invention also provides a method for the cosmetic treatment of the skin, by the topical route, by applying a composition as defined above to the skin, face, scalp and/or human body. The type of treatment depends on the active agent(s) dissolved in the composition.

More especially, the present invention provides a method for preventing and/or controlling pigmentation of the skin or for controlling greasy skin and/or excessive weight by applying, to the skin, a composition as defined above containing at least one depigmenting active agent or active agent for controlling pigmentation, at least one slimming active agent or at least one active agent for treating greasy skin.

A further subject of the present invention is the use of the above composition for treating the skin of the face and/or of the human body and especially for preventing and/or controlling pigmentation of the skin and/or for controlling greasy skin of the face, of the scalp and/or of the human body and for preventing and/or controlling excessive weight.

A further subject of the present invention is the use of the above composition for preparing a salve or an ointment intended for the therapeutic treatment of the face and/or the human body.

Other features of the invention will become apparent in the course of the following descriptions of exemplary embodiments which are given for illustration of the invention and are not intended to be limiting thereof.

EXAMPLES

The concentrations of the various constituents forming part of the compositions exemplified below are given as percentages by weight, based on the total weight of the composition. These various compositions are obtained according to the following procedure.

The active agent(s) is/are dissolved in the chosen solvent or mixture of solvents (Phase A) and then gelling is carried out with the copolymer (Phase C) by simple homogenization at room temperature by means of a propeller turbine. Expanded hollow microspheres are thickened with the emollient oils (Phase B) when the oils are present. The mixture is then incorporated, still at room temperature, with the same means. In the case where there is no emollient oil, the expanded hollow microspheres are sprinkled in at the end and incorporated by means of a paddle. The formulae are either fluid and not free-running or with a flow threshold such that the product does not flow under its own weight. They have the appearance of a homogeneous, smooth, glossy, oily and supple cream.

In the examples which follow, the amounts are given as percentages by weight, based on the total weight of the composition, and the term "q.s. for 100%" means that that component is present in an amount such that the sum of the amounts for all components equals 100% by weight.

Example 1
Depigmenting Cream

| Phase A | |
|---|---|
| Demineralized water | q.s. for 100% |
| Ethyl alcohol at 96% in water | 30% |
| Polyethylene glycol oxyethylenated 8 times | 30% |
| Caffeic acid | 1.2% |
| Salicylic acid | 5% |
| Phase B | |
| Expancel EL 23 | 0.5% |
| Liquid fraction of karite butter | 2% |
| Phase C | |
| Gelling agent* | 5% |
| Phase D | |
| Dye, fragrance | q.s. |

The product obtained has the appearance of a yellow, opaque, smooth, glossy and stable cream. Its pH is 3.

Example 2
Depigmenting Cream

| Phase A | |
|---|---|
| Demineralized water | q.s. for 100% |
| Ethyl alcohol at 96% in water | 30% |
| Polyethylene glycol oxyethylenated 8 times | 30% |
| Caffeic acid | 1.2% |
| 5-(n-Octanoyl)salicylic acid | 2% |
| Phase B | |
| Expancel EL 23 | 0.5% |
| Liquid fraction of karite butter | 2% |
| Phase C | |
| Salcare 95 Gelling agent | 6% |
| Phase D | |
| Dye, fragrance | q.s. |

The product obtained has the appearance of a yellow, opaque, smooth, glossy and stable cream. Its pH is 3.

Example 3
Slimming Cream

| Phase A | |
|---|---|
| Demineralized water | q.s. for 100% |
| Ethyl alcohol at 96% in water | 30% |
| Caffeine | 2% |
| Phase B | |
| Expancel EL 23 | 1% |
| Oily extract of English ivy | 5% |
| Phase C | |
| Gelling agent* | 2% |
| Lubrajel ® by the Company Gaurdian | 20% |

The product obtained has the appearance of a white, smooth, glossy and stable cream. Its pH is 6.

(*) This gelling agent corresponds, in Examples 1 and 3, to the product as prepared in Example 1 of the already mentioned Patent Application EP-A-0,503,853, that is to say a product which is provided in the form of an emulsion of water-in-oil type and which contains approximately 40% by weight of a crosslinked acrylamide (60 mol %)-sodium AMPS (40 mol %)-methylene-bisacrylamide (0.22 millimol/mol) copolymer and approximately 60% by weight of an ethoxylated fatty alcohol having a value of the hydrophile/lipophile balance (HLB).

Example 4
Cream for Greasy Skins

| Phase A | |
|---|---|
| Demineralized water | q.s. for 100% |
| Ethyl alcohol at 96% in water | 30% |
| Polyethylene glycol oxyethylenated 8 times | 30% |
| Octopirox | 0.5% |
| Phase B | |
| 551 DE 20 | 1% |
| Cyclohexadimethylsiloxane | 5% |
| Phase C | |
| Carbopol 980 | 0.5% |
| Water | 20% |
| Phase D | |
| Triethanolamine | q.s. for pH = 7 |

The product obtained has the appearance of a glossy, oily and soft cream.

This application is based on French patent application 94-08568 filed Jul. 11, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A cosmetic and/or dermatological composition having a homogeneous appearance comprising a hydrophilic medium, at least one gelling agent, and hollow particles having a density of up to 200 kg/m$^3$, wherein said medium comprises at least 20% by weight of an organic solvent, based on the total weight of said composition, and less than 50% by weight of water, based on the total weight of said composition.

2. The composition of claim 1, wherein said particles have a density not greater than 120 kg/m$^3$.

3. The composition of claim 1, wherein said particles have a density ranging from 40 kg/m$^3$ to 100 kg/m$^3$.

4. The composition of claim 1, wherein said particles have a density ranging from 60 kg/m$^3$ to 80 kg/m$^3$.

5. The composition of claim 1, wherein said particles have an average particle size ranging from 5 μm to 200 μm.

6. The composition of claim 1, wherein said particles have an average particle size ranging from 10 μm to 100 μm.

7. The composition of claim 1, wherein said particles have an average particle size ranging from 10 μm to 50 μm.

8. The composition of claim 1, wherein said particles are microspheres formed from an expanded polymer or copolymer of methyl (meth)acrylate and/or of acrylonitrile and/or of vinylidene chloride.

9. The composition of claim 1, wherein said particles are present in an amount of from 0.01% to 10% by weight, based on the total weight of said composition.

10. The composition of claim 1, wherein said hydrophilic medium comprises less than 30% by weight of water, based on the total weight of said composition.

11. The composition of claim 1, wherein said hydrophilic medium comprises at least one organic solvent selected from the group consisting of mono- or polyfunctional alcohols, optionally oxyethylenated polyethylene glycols, propylene glycol esters, sorbitol, dialkyl ethers of isosorbide, glycol ethers, and propylene glycol ethers.

12. The composition of claim 1, wherein said organic solvent comprises a hydrophilic solvent which is present in an amount of from 5% to 90% by weight, based on the total weight of said composition.

13. The composition of claim 1, wherein said gelling agent is present in an amount of from 0.1% to 10% by weight, based on the total weight of said composition.

14. The composition of claim 1, further comprising at least one oil which is soluble or insoluble in the hydrophilic medium.

15. The composition of claim 14, wherein said oil is present in an amount of up to 50% by weight, based on the total weight of said composition.

16. The composition of claim 1, further comprising at least one cosmetically and/or dematologically acceptable active agent.

17. The composition of claim 1, further comprising at least one depigmenting or slimming active agent or active agent for treating greasy skins.

18. The composition of claim 1, further comprising at least one additive selected from the group consisting of ceramides, preserving agents, antioxidizing agents, emollients, and fragrances.

19. The composition of claim 1, further comprising at least one active agent selected from the group consisting of caffeic acid, salicylic acid, 5-(n-octanoyl)salicylic acid, caffeine, octopirox, and mixtures thereof.

20. The composition of claim 1, which is in the form of a salve or an ointment.

21. A method for controlling pigmentation of the skin or for controlling greasy skin, comprising applying to the skin a composition having a homogeneous appearance which comprises a hydrophilic medium, at least one gelling agent, and hollow particles having a density of up to 200 kg/m$^3$, wherein said medium comprises at least 20% by weight of an organic solvent, based on the total weight of said composition, and less than 50% by weight of water, based on the total weight of said composition.

22. A method for cosmetically treating the skin of the face, of the scalp and/or of the human body, comprising applying, to the skin, a composition which has a homogeneous appearance, said composition comprising a hydrophilic medium, at least one gelling agent, and hollow particles having a density of up to 200 kg/m$^3$, wherein said medium comprises at least 20% by weight of an organic solvent, based on the total weight of said composition, and less than 50% by weight of water, based on the total weight of said composition.

* * * * *